United States Patent [19]

Shaw et al.

[11] 4,314,075

[45] Feb. 2, 1982

[54] PROCESS FOR THE PRODUCTION OF OLEFINIC ACIDS AND ESTERS

[75] Inventors: Wilfrid G. Shaw, Lyndhurst; Philip L. Kuch, Aurora; Christos Paparizos, Willowick, all of Ohio

[73] Assignee: The Standard Oil Company, Cleveland, Ohio

[21] Appl. No.: 184,592

[22] Filed: Sep. 5, 1980

[51] Int. Cl.³ .................... C07C 51/377; C07C 57/05; C07C 67/317; C07C 69/54

[52] U.S. Cl. .................................... 562/599; 252/435; 252/436; 252/437; 560/214; 568/397

[58] Field of Search ................. 560/214; 562/599; 252/435–437; 260/405.5

[56] References Cited

U.S. PATENT DOCUMENTS

| | | | |
|---|---|---|---|
| 3,917,673 | 11/1975 | Watkins | 562/599 |
| 4,061,673 | 12/1977 | Onoda et al. | 562/599 |
| 4,081,465 | 3/1978 | Gruber et al. | 562/599 |
| 4,232,174 | 11/1980 | Statz et al. | 562/599 |

FOREIGN PATENT DOCUMENTS 48-19614  6/1973  Japan .................................. 562/599

Primary Examiner—Vivian Garner
Attorney, Agent, or Firm—Gary R. Plotecher; Herbert D. Knudsen; Larry W. Evans

[57] ABSTRACT

Olefinic acids and esters, such as methacrylic acid and methylmethacrylate, are prepared by contacting in the presence of molecular oxygen the corresponding saturated acid or ester, such as isobutyric acid or methylisobutyrate with the catalyst of the empirical formula:

$$Mo_{12}P_{0.1-3}M_{0.1-3}Cu_{0.01-2}V_{0.01-2}X_{0.01-2}M'_aO_b \quad \text{(I)}$$

where
M is at least one of K, Rb and Cs;
X is at least one of Ba, La, Ga, Al, Ag, Cd, Ti, Tl, Hg, Pb and Zn;
M' is at least one of Fe, Co, Ni, Sr, Mn, In, Ta, Ge, S and Be when a >0;
a is a number of 0 to about 2; and
b is a number that satisfies the valence requirements of the other elements present.

12 Claims, No Drawings

PROCESS FOR THE PRODUCTION OF OLEFINIC ACIDS AND ESTERS

BACKGROUND OF THE INVENTION

FIELD OF THE INVENTION

This invention relates to catalysis. In one aspect, the invention relates to the catalytic oxydehydrogenation of lower saturated acids and esters to the corresponding unsaturated acids and esters while in another aspect, the invention relates to the use of heteropolyacids containing molybdenum, phosphorus, alkali metal, copper, vanadium and certain promoters as the catalyst.

DESCRIPTION OF THE PRIOR ART

U.S. Pat. No. 3,917,673 teaches the synthesis of unsaturated lower aliphatic acids and esters by the catalytic oxidative dehydrogenation of the corresponding saturated acids and esters. The catalyst is the calcined residue of the mixture of bismuth oxynitrate, iron phosphate and lead phosphate.

U.S. Pat. No. 4,061,673 teaches the vapor-phase manufacture of methacrylic acid by the oxidative dehydrogenation of isobutyric acid in the presence of a supported acid containing a heteropolyacid and/or a reduced form of the heteropolyacid. The catalyst contains molybdenum, tungsten, vanadium, phosphorus and oxygen and is supported on a carrier that has a silicon dioxide content of at least 70%.

Other methods of preparing olefinic acids and esters by the oxidative dehydrogenation of the corresponding saturated acids and esters are also known. Representative of these are BE No. 848,300, DT No. 2,438,464 and JAP Nos. 3,082,720, 2,105,112, 2,105,113, 1,118,718, 2,039,622 and 2,631,018.

SUMMARY OF THE INVENTION

According to this invention, lower, saturated aliphatic acids and esters are oxydehydrogenated to the corresponding olefinic acids and esters by a process comprising contacting in the presence of molecular oxygen the vaporous, saturated acid or ester with a catalyst of the empirical formula $$Mo_{12}P_{0.1-3}M_{0.1-3}Cu_{0.1-2}V_{0.1-2}X_{0.01-2}M'_aO_b \quad (I)$$

where
M is at least one of K, Rb and Cs;
X is at least one of Ba, La, Ga, Al, Ag, Cd, Ti, Tl, Hg, Pb and Zn;
M' is at least one of Fe, Co, Ni, Sr, Mn, In, Ta, Ge, S and Be when a>0;
a is a number of 0 to about 2; and
b is a number that satisfies the valence requirements of the other elements present.

The process gives a good single pass conversion of the saturated acid or ester and a good selectivity to the olefinic acid or ester product. The invention is particularly useful for the manufacture of methacrylic acid from isobutyric acid.

DETAILED DESCRIPTION OF THE INVENTION

Lower, saturated aliphatic acids and esters are the starting materials of this invention. Representative of these materials are compounds of the formula

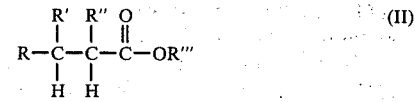

where R—R''' are independently hydrogen or a $C_1$–$C_4$ alkyl radical. The acids (R''' is hydrogen) are preferred to the esters and the acids where R and R' are hydrogen are the preferred acids. Isobutyric acid (R, R' and R''' are hydrogen and R'' is methyl) is a preferred starting material. The acids and esters here used can contain inert substituents, i.e. substituents that are essentially nonreactive with the starting materials, catalysts and products and the process at process conditions, but preferably the starting acids and esters are free of these substituents.

The molecular oxygen can be used in essentially pure form or diluted with other gases, such as nitrogen, carbon dioxide, water vapor, helium, argon, various mixtures of these gases etc. For reasons of economy and convenience, the molecular oxygen is generally used in the form of air.

The catalysts of this invention, as evidenced from formula I, comprise at least seven elements, i.e. molybdenum, phosphorus, alkali metal (M), copper, vanadium, oxygen and at least one metal X all present in designated, proportional amounts. Preferably, the subscript value of phosphorus in formula I is about 0.5 to 1.75, of alkali metal (M) about 0.8 to 2, of copper about 0.1 to 0.8, of vanadium about 0.1 to 0.8, and of X about 0.02 to 0.5. The exact structure or element arrangement of these catalysts is not known but the metal and phosphorus components are present in the form of their oxides, acids or oxide or oxyacid complexes. However, the compositions of formula I are known not to be a mere physical mixture of their components, but rather unique, heteropolyacid entities where the individual components are chemically and/or physically bonded to one another.

Preferred catalysts are those where X is barium, mercury, thallium, zinc or lead and most preferred catalysts are those where X is barium, mercury or lead. In these preferred catalysts, M is typically rubidium or potassium. These catalysts can also include yet another component, here designated M'. When component M' is present (a>0), it is generally as iron, cobalt, tantalum or germanium.

As taught by formula I, certain of the components can be combinations of two or more elements, e.g., X can be a combination of barium and zinc. In such instances, the subscript value represents the sum of the elements (e.g. for X, the sum of barium and zinc is a number of about 0.01 to 2). Generally, M, X, and M' each represent but a single element.

Particularly preferred catalytic compositions are seven element or component (including oxygen) catalysts where M is rubidium or potassium, X is barium, moiety or lead and a is 0.

The catalytic compositions of this invention can be used in either the 100% active form or in a diluted form, i.e. supported or unsupported. Suitable support materials include silica, titania, alumina, zirconia, silicon carbide, boron, various phosphates, etc. with low surface area (about 1 m²/g) alumina a preferred support material. If a support is used, the catalytic composition is generally present in an amount of at least about 20 weight percent, based upon the combined weight of the support and catalytic composition, and preferably in an amount of at least 30 weight percent.

The catalytic compositions of this invention can be prepared by any one of a number of different methods, the particular method employed being a matter of convenience. Typically, the catalysts are prepared by mixing the appropriate catalyst ingredients in the proper proportion in an aqueous mixture, drying the resulting aqueous slurry with or without a reducing agent, and subsequently calcining the product. The ingredients can be added in any order during the preparation procedure but certain orders are preferred, particularly the mixing of the metallic ingredients prior to the addition of phosphorus (generally in the form of phosphoric acid). The ingredients employed can be the oxides, halides, nitrates, acetates or other salts of the particular metals or elements added, and particularly preferred is the use of water soluble salts of the metal components. If a support is used, the materials comprising the support may be incorporated into the catalyst along with the other ingredients or the catalytic composition may be coated and/or impregnated onto or into a core. After the catalyst ingredients have been combined to form an aqueous slurry, the slurry is taken to dryness and a dried solid obtained is heated in the presence of air, nitrogen, nitric oxide or a mixture of any two or more of these gases at a temperature between about 300° and 420° C. This calcination can take place outside the catalytic reactor or an in situ activation can be utilized. Other methods of preparation are broadly taught in the art.

The process of this invention is a vapor phase process, i.e., gaseous starting materials are contacted with a solid catalyst. The process can be conducted at any temperature in which the starting acid or ester and molecular oxygen are in gaseous form and typically the process is conducted at a temperature between about 270° and 355° C. A preferred temperature is between about 285° and 345° C. Likewise, the reaction can be conducted at any pressure at which the starting materials are in a gaseous form and thus subatmospheric, atmospheric and superatmospheric pressures can be employed. For reasons of economy and convenience, autogenous pressures are preferred.

The molar ratio of oxygen to starting acid or ester can vary widely with molar ratios of 0.5 to about 3 being typical. As noted earlier, the gaseous feed mixture can be diluted with a carrier gas, such as nitrogen, carbon dioxide, water vapor, etc.

Sufficient catalyst is used to insure adequate opportunity for the gaseous starting materials to contact the catalyst surface. The contact time can range from a fraction of a second to several hours or more but preferably, the contact time ranges from about 0.1 sec to about 10 sec.

The products of this invention are the corresponding olefinic acids and esters. These materials are represented by the formula

where the various substituents are defined as for formula II. These materials have a wide range of utility in the plastics and paint industries.

The following examples are illustrative of certain specific embodiments of this invention. Unless otherwise indicated, all parts and percentages are by weight.

SPECIFIC EMBODIMENTS

Catalyst Preparation

The catalyst used in the following examples are prepared by dissolving, with stirring, ammonium heptamolybdate in distilled water and heating the resulting solution to 30°–35° C. While continuously stirring and maintaining the temperature, potassium hydroxide and barium hydroxide were added. After 15 min, copper acetate and ammonium metavanadate solutions were added followed by a hydrochloric acid solution. The resulting slurry was then heated to 70° C. for two hours. Subsequently, phosphoric acid was added. Stirring and heating were then continued for about 30 min followed by a pH adjustment to 5.6. The mixture was evaporated to a thick paste and then dried in an oven at 110°–120° C. The dried product was then reduced to a powder of less than 50 mesh (U.S. standard) and the resulting powder was coated onto ⅛ in Alundum ® spheres (alumina) such that the coating constituted about 35 weight percent of the coated spheres. The catalyst had the composition:

PROCESS PROCEDURE AND CONDITIONS

The examples were conducted in a 20 cc downward flow, fixed-bed reactor. All runs were performed in the same manner: one hour at 370° C. with air flow (no feed) followed by about two hours at the reaction temperature with air flow plus feed to equilibrate the catalyst. After the equilibrium period, an example was conducted for 20 min to obtain sufficient reactor effluent for analysis. Off-gas rate was measured with a soap-film meter and the off-gas composition was determined at the conclusion of each run with the aid of a Perkin-Elmer 154 gas chromatograph. At the end of each run the entire scrubber liquid was diluted with distilled water to about 100 g. A weighed amount of methanol was used as an internal standard in a 20 g aliquot of the diluted solution. A one microliter sample was analyzed in a Hewlett-Packard 5710A gas chromatograph fitted with a flame ionization detector and a SB 1200 column. The splits between methacrylic, acrylic and acetic acid were determined by gas chromatographic analysis. Other reaction conditions and reaction results are reported in Table I.

TABLE I

| | | | | | | Corrected Per Pass Conversion | | | | | | | | |
|---|---|---|---|---|---|---|---|---|---|---|---|---|---|---|
| Example | Temp (°C.) | Feed IBA/AIR/H₂O (Moles) | Contact Time (sec) | WWH[5] | MAA[1] | Acetone | CO | CO₂ | C₃ | Unr. IBA[4] | Sel. MMA[3] | Carbon Balance | Conver.[2] | O₂ in Effluent (mole %) |
| 1 | 327 | 1/4.0/25.3 | 1.1 | 0.25 | 67.3 | 12.5 | 7.0 | 2.3 | 1.8 | 3.2 | 69.5 | 95.1 | 96.8 | 8.5 |
| 2 | 327 | 1/4.3/18.3 | 1.4 | 0.25 | 68.6 | 12.0 | 7.4 | 3.0 | 6.9 | 2.1 | 70.1 | 105.8 | 97.9 | 6.3 |
| 3 | 322 | 1/4.0/12.1 | 1.9 | 0.25 | 66.1 | 11.9 | 9.1 | 4.4 | 6.0 | 2.5 | 67.8 | 95.5 | 97.5 | 3.3 |

TABLE I-continued

OXYDEHYDROGENATION OF ISOBUTYRIC ACID

| Example | Temp (°C.) | Feed IBA/AIR/H$_2$O (Moles) | Contact Time (sec) | WWH[5] | MAA[1] | Acetone | CO | CO$_2$ | C$_3$ | Unr. IBA[4] | Sel. MMA[3] | Carbon Balance | Conver.[2] | O$_2$ in Effluent (mole %) |
|---|---|---|---|---|---|---|---|---|---|---|---|---|---|---|
| | | | | | | Corrected Per Pass Conversion | | | | | | | | |
| 4 | 322 | 1/4.0/12.1 | 1.9 | 0.25 | 66.5 | 11.6 | 8.8 | 4.4 | 6.0 | 2.7 | 68.4 | 95.9 | 97.3 | 3.4 |
| 5 | 322 | 1/4.0/18.3 | 1.4 | 0.25 | 68.2 | 12.1 | 8.0 | 3.5 | 6.4 | 1.9 | 69.5 | 98.9 | 98.1 | 5.5 |
| 6 | 313 | 1/4.0/18.3 | 1.4 | 0.25 | 64.6 | 12.2 | 6.1 | 3.4 | 6.0 | 7.8 | 70.0 | 107.8 | 92.2 | 6.1 |
| 7 | 316 | 1/4.0/18.3 | 1.4 | 0.25 | 64.9 | 12.2 | 7.9 | 3.8 | 6.2 | 3.1 | 69.1 | 92.3 | 96.9 | 5.9 |

[1] Methacrylic Acid Yield = Moles of Methacrylic Acid Recovered × 100/Moles of Isobutyric Acid
[2] Isobutyric Acid Conversion = Moles of Isobutyric Acid Reacted × 100/Moles of Isobutyric Acid
[3] Methacrylic Acid Selectivity = Methyacrylic Acid Yield × 100/Isobutyric Acid Conversion
[4] Unreacted Isobutyric Acid
[5] Weight of Isobutyric Acid per Weight of Catalyst Per Hour Although the invention has been described in considerable detail through the preceding examples, these examples are for the purpose of illustration only and it is understood that variations and modifications can be made by one skilled in the art without departing from the spirit and scope of the invention.

What is claimed is:

1. A vapor-phase process for the production of a compound of the formula $$R-\underset{\underset{}{}}{\overset{R'}{C}}=\underset{\underset{}{}}{\overset{R''}{C}}-\overset{O}{\overset{\|}{C}}-OR''' \quad (III)$$

the process comprising contacting in the presence of molecular oxygen a compound of the formula $$R-\underset{\underset{H}{|}}{\overset{R'}{\overset{|}{C}}}-\underset{\underset{H}{|}}{\overset{R''}{\overset{|}{C}}}-\overset{O}{\overset{\|}{C}}-OR''' \quad (II)$$

where R-R''' are independently hydrogen or a C$_1$-C$_4$ alkyl radical, with a catalytic amount of a catalyst of the formula $$Mo_{12}P_{0.1-3}M_{0.1-3}Cu_{0.1-2}V_{0.1-2}X_{0.01-2}M'_aO_b \quad (I)$$

where

M is at least one of K, Rb and Cs;
X is at least one of Ba, La, Ga, Al, Ag, Cd, Ti, Tl, Hg, Pb and Zn;
M' is at least one of Fe, Co, Ni, Sr, Mn, In, Ta, Ge, S and Be when a>0;
a is a number of 0 to about 2; and
b is a number that satisfies the valence requirements of the other elements present.

2. The process of claim 1 where M is K or Rb.
3. The process of claim 2 where X is Ba, Hg, Tl, Pb or Zn.
4. The process of claim 2 where X is Ba, Hg or Pb.
5. The process of claim 4 where a is 0.
6. The process of claim 4 where a>0.
7. The process of claim 6 where M' is Fe, Co, Ta or Ge.
8. The process of claim 7 where the subscript value of P in formula I is about 0.5 to 1.75, of M about 0.8 to 2, of Cu about 0.1 to 0.8, of V about 0.1 to 0.8 and of X about 0.02 to 0.5.
9. The process of claim 8 where the catalyst is diluted with a support.
10. The process of claim 9 where the support is a low surface area alumina.
11. The process of claim 10 where the compound of formula II is isobutyric acid.
12. The process of claim 8 where the catalyst is unsupported.

* * * * *